United States Patent [19]
Mendoza et al.

[11] Patent Number: 5,147,299
[45] Date of Patent: Sep. 15, 1992

[54] DEVICE TO FACILITATE ARTIFICIAL INSEMINATION OF BOVINES AND SIMILAR ANIMALS

[76] Inventors: Marco A. H. Mendoza, Rebsamen 573, Col. Narvarte, 03020; Malcolm Niven, Montes Urales 625, Lomas de Chapultepec, 11000, both of Mexico

[21] Appl. No.: 471,213

[22] Filed: Jan. 29, 1990

[30] Foreign Application Priority Data

Jan. 31, 1989 [MX] Mexico ........................... 14076

[51] Int. Cl.$^5$ ........................................... A61M 29/00
[52] U.S. Cl. ................................. 604/96; 606/192
[58] Field of Search ............................ 604/96–101, 604/906, DIG. 1, 55; 128/207.14, 207.15, 207.16, 207.17; 606/191, 195

[56] References Cited

U.S. PATENT DOCUMENTS

| | | | |
|---|---|---|---|
| 3,889,676 | 6/1975 | Greene | 604/101 |
| 4,301,797 | 11/1981 | Pollack | 604/101 |
| 4,305,392 | 12/1981 | Chester | 604/98 |
| 4,324,235 | 4/1982 | Beran | 604/96 |
| 4,335,723 | 6/1982 | Patel | 604/100 |
| 4,654,025 | 3/1987 | Casson et al. | 604/101 |

FOREIGN PATENT DOCUMENTS 154491  7/1987  Mexico .

Primary Examiner—C. Fred Rosenbaum
Assistant Examiner—William Lewis
Attorney, Agent, or Firm—Henry P. Sartorio

[57] ABSTRACT

The addition of one or more lateral ejecting holes in the end of the insemination device that is introduced into the entrance of the neck of the uterus of the cow, for depositing semen, will permit a better application of the semen and also will allow the device to be used not only for the insemination of bovines, but also for other animals of different species whose sexual anatomical characteristics are similar to those of cows, by adapting the size of the device to the particular characteristics of the other animals.

7 Claims, 3 Drawing Sheets

DEVICE TO FACILITATE ARTIFICIAL INSEMINATION OF BOVINES AND SIMILAR ANIMALS

FOREIGN PRIORITY

This application claims priority of Mexican patent application No. 14720/14076 filed Jan. 31, 1989.

BACKGROUND OF THE INVENTION

The invention relates to the artificial insemination of bovines and other animals.

The device to facilitate the artificial insemination of cows, that has been described in Mexican patent No. 154491, has proved to be a great advancement in artificial insemination, reducing time, expenses and effort, in the training and availability of expert inseminators, surpassing to a great extent the traditional practices used for insemination and increasing its effectiveness.

The aforementioned patent covers a device to facilitate the artificial insemination of cows, that includes a seal forming means in the form of a combination of a solid or an inflatable small balloon mounted on a small tube approximately 4 cm long, open at both ends. An ordinary inseminating pipette, through which the semen is introduced using a syringe, is inserted in the rear end of the tube. In operation the seal forming means provide a seal at the neck of the uterus so that semen can be injected through the pipette without discharge back. The device is also characterized by a flexible hose of one or two millimeters in diameter, attached at one of its ends to the small tube that is covered by the sleeve that forms the inflatable balloon and at the other end it is attached to another syringe to inject air to inflate the balloon. The inflation means are of course eliminated with the rigid balloon.

A problem with the above described artificial insemination device is that the device has only a single ejection hole at its tip. Depending on the position of the device within the animal's uterus, the tip may be pressed against the uterine wall, or the hole may be otherwise become plugged, blocking the discharge of the semen. Thus an insemination device with an improved discharge of semen is desirable.

SUMMARY OF THE INVENTION

Accordingly it is an object of the invention to provide an artificial insemination device for bovines with improved semen discharge.

It is also an object of the invention to provide a device that can be adapted to other animals.

The invention, that will improve the aforementioned patent, has the purpose of achieving an easier injection of the semen contained in the pipette of the inseminating device, into the uterus of the cow, eliminating the inconveniences, in some cases, of the difficulty in passing the semen through the only hole in the ejecting end of the device; and also to allow it to be used with the same inseminating results in other animals of similar sexual structure as bovines. The invention comprises at least one, and preferably a plurality, of lateral ejection ports or holes formed in the tip of the insemination device. These lateral ports proved a wider semen discharge pattern which is not obstructed even if the end of the tip is blocked.

The characteristic details of this improvement are shown clearly in the following description and drawings, as an illustration, using the same reference numerals to indicate the same parts in the figures.

DETAILED DESCRIPTION OF THE PREFERRED EMBODIMENTS

Figure 1:
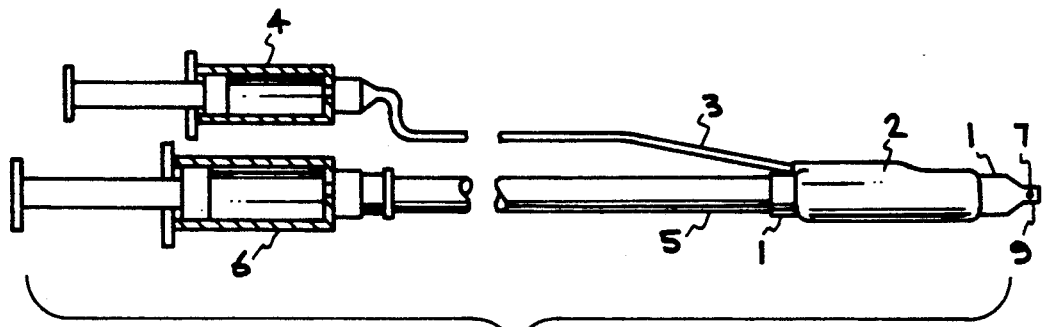
FIGS. 1 and 4 show an external side view of the device.
Figure 2:
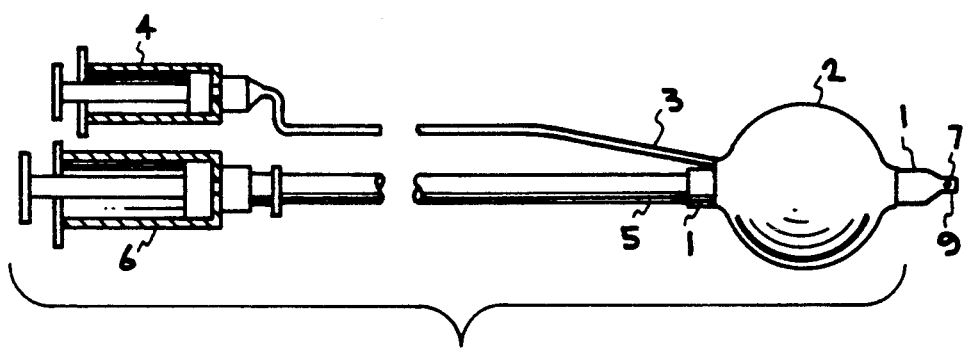
FIG. 2 is a side view of the device showing the inflated balloon.
Figure 3:
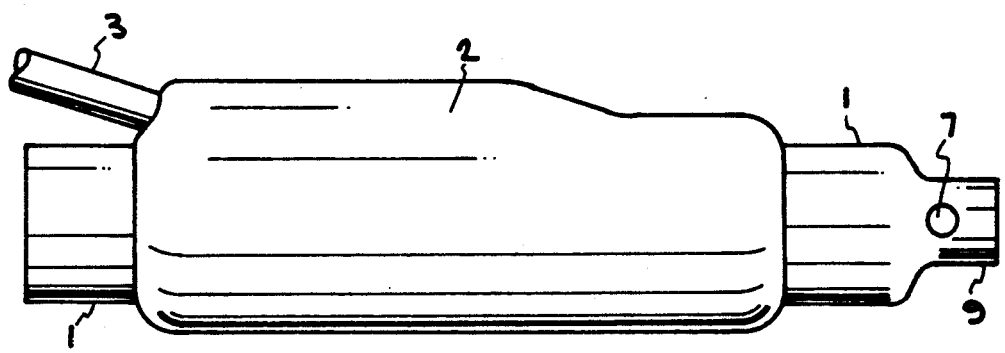
FIG. 3 is an amplified view of the tip and inflatable sealing means of the device.
Figure 4:
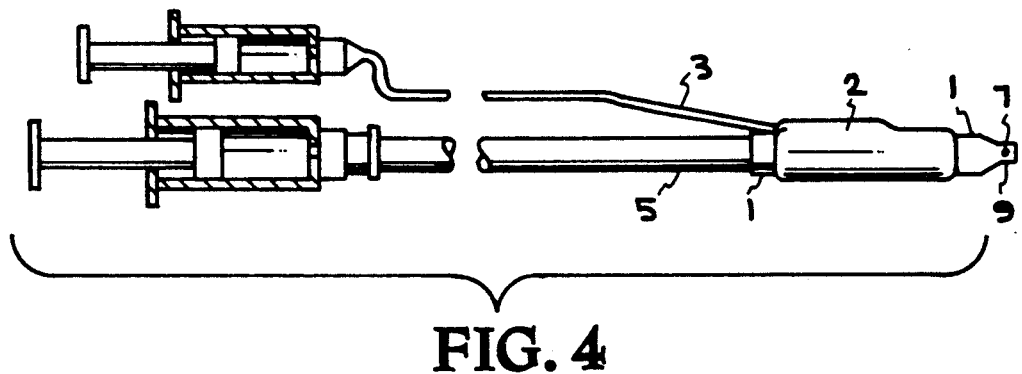

With reference to such views, this device is formed by a rigid tube 1, about 4 cm long and 5 mm in diameter, enclosed by a rubber sleeve 2 that takes the shape of a balloon when inflated through a thin hose 3 placed between the rigid tube and the rubber sleeve with the purpose of inflating the rubber balloon. The thin hose extends backwards to terminate in a connector for a syringe 4 to introduce the air to inflate the balloon with the syringe. Alternatively a balloon made of rigid rubber is mounted on the rigid tube and does not need to be inflated, and will appear as in FIG. 2 without hose 3 and syringe 4.

The device is placed (attached in any suitable manner) on the front part of an inseminating pipette 5. The pipette passes into the interior of tube 1 which is attached on the tip of the inseminating pipette. In operation, the pipette has been previously loaded with the semen and diluting liquid, and is connected, at the opposite end of the pipette from the tube 1, to a syringe 6 that will push with air the semen (and diluting fluid) contained in the pipette into the uterus of the animal as is described in Mexican patent No. 154491.

In operation, a speculum is introduced through the vagina to locate the neck of the uterus. Once the neck is located, the whole assembly is introduced loaded with semen, with the device at its anterior tip, and the balloon is inflated to seal hermetically the neck. Then the inseminating pipette is discharged, pushing towards the uterus the semen contained, as a result of the pressure of the air that is pushed with the syringe connected to the opposite end of the pipette. In this way the semen will reach the uterus, pushed by the pressure of the diluting liquid, and will not return to the vagina as the neck is hermetically sealed with the inflated balloon, or alternatively with the solid balloon pressed against the neck.

Figure 5:
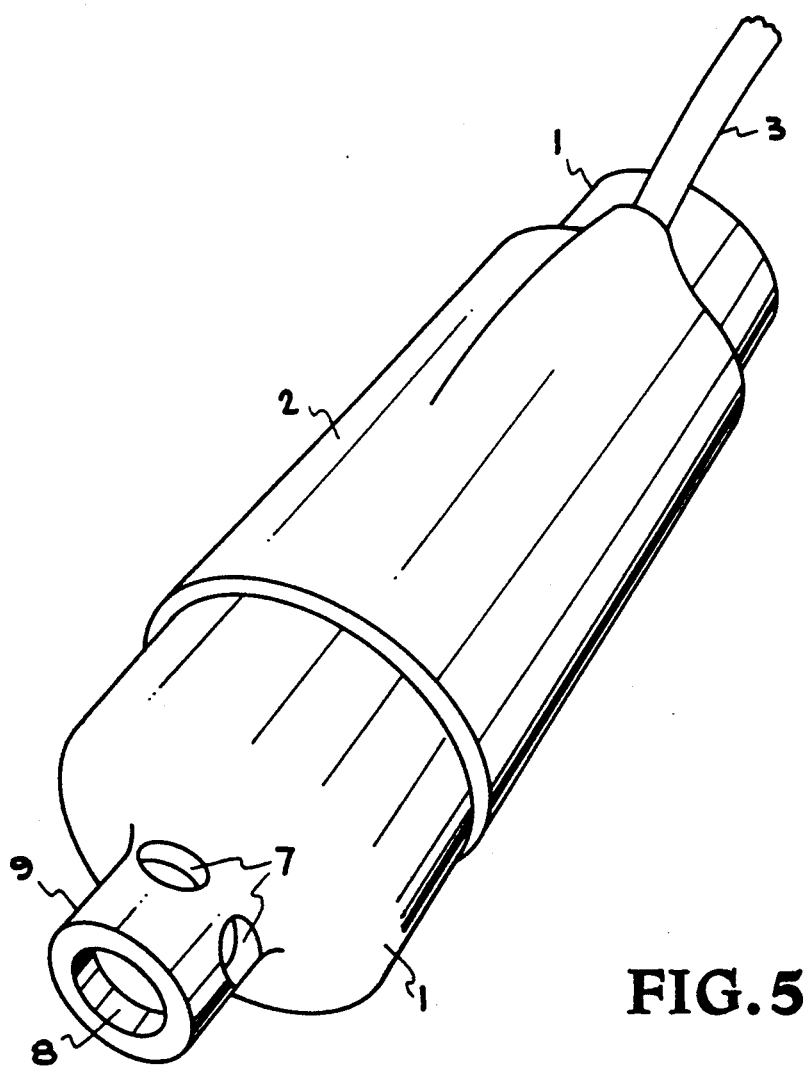
FIG. 5 is a perspective view of the tip and inflatable sealing means of the device.
Figure 6:
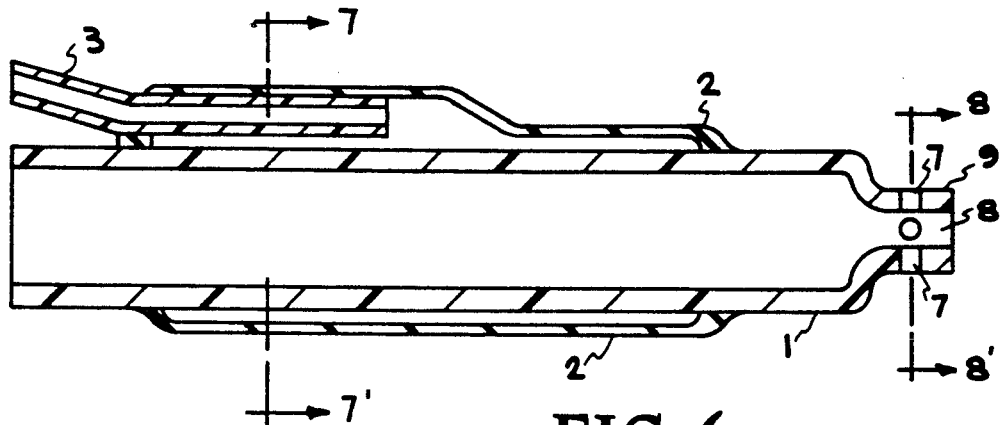
FIG. 6 is a vertical projection of a longitudinal section of the device.
Figure 7:
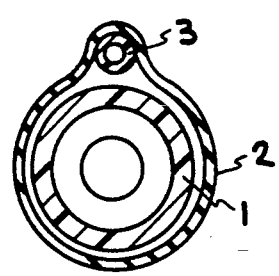
FIG. 7 is another vertical projection of a transverse section of FIG. 6 at 7—7' to show the anterior interior mechanism of the device.
Figure 8:
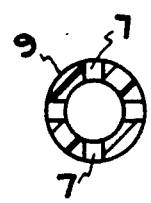
FIG. 8 shows the transverse section of the tip of the device, front view, of FIG. 6 at 8—8'.
Figure 9:
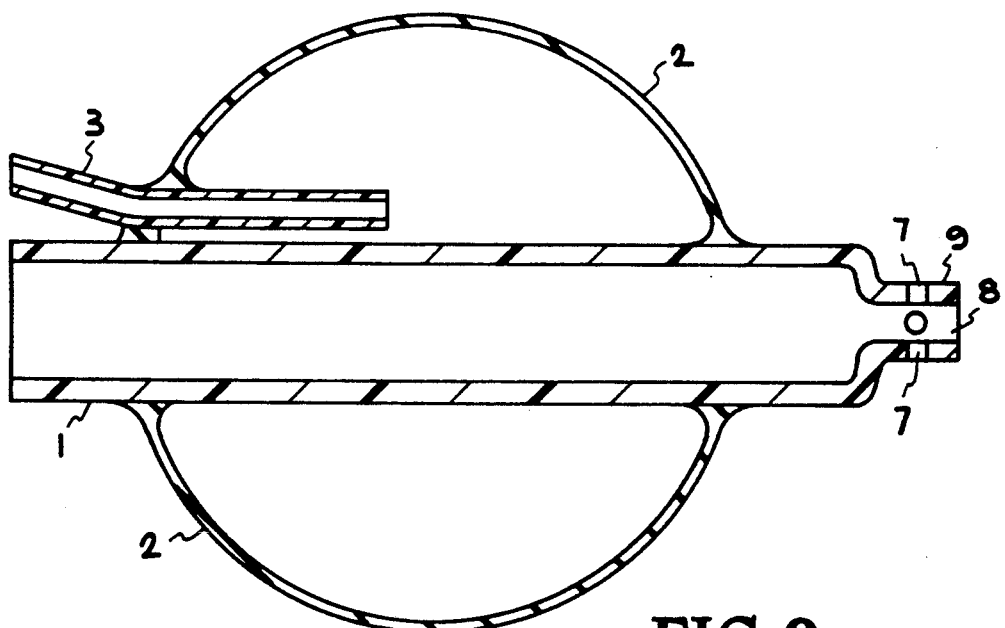
FIG. 9 is a vertical projection of a longitudinal section of the device when the balloon is inflated.

The improvement of the device is one or more lateral ejection ports or holes 7 formed near the tip of tube 1 through which the semen is ejected toward the uterus of the animal. In the aforementioned patent there is only one ejecting hole 8 that is located in the tip of the device, i.e. the open end of the tube 1 forms the only ejection port; this makes the fast ejection of the semen difficult in some cases. Therefore, the improvement consists of adding one or more lateral holes 7, preferably a plurality, as shown particularly in FIG. 5; this will permit a smooth and fast ejection of the semen towards the uterus and will permit inseminating other animals besides bovines.

Although the rigid tube 1, which is attached to the end of the inseminating pipette 5 and carries the seal forming means 2, may be of a constant diameter, tube 1 preferably has a tip portion 9 of narrower diameter in which lateral ejection ports 7 are formed to recess ports 7 from the larger diameter of tube 1 to further improve the discharge pattern and characteristics. Alternatively, instead of forming a separate tube 1 which is attached to pipette 5, the seal forming means could be mounted directly on pipette 5 and lateral ejection ports 7 could be formed at the distal end of pipette 5, thus eliminating the need of a separate tube 1.

There is another important improvement of the device and it consists in varying the size of the device to be used in the artificial insemination of animals of other species, besides bovines. The inseminating process is similar to the process used in bovines, modifying the size of the device according to the anatomical characteristics of the animal species to be inseminated. Thus the invention includes forming the devices of predetermined size for a particular animal species.

Changes and modifications in the specifically described embodiments can be carried out without departing from the scope of the invention which is intended to be limited only by the scope of the appended claims.

We claim:

1. Apparatus to facilitate the artificial insemination of bovines and similar species, comprising:
    a conventional semen injecting insemination pipette for bovines through which semen will be introduced with a syringe;
    a rigid tube having a diameter greater than the diameter of the pipette fitted over and attached to the distal end of the pipette;
    seal forming means attached to the rigid tube;
    an insemination tip formed at the distal end of the rigid tube and having a diameter less than the diameter of the pipette so that the distal end of the pipette extending into the tube abuts the tip, the insemination tip having an open ejection port at its end;
    at least one lateral ejection port formed on a lateral side of the insemination tip;
    wherein the rigid tube is about 4 cm long and about 5 mm in diameter.

2. The apparatus of claim 1 wherein the seal forming means is an inflatable balloon, and further comprising means to inflate the balloon attached to the balloon.

3. The apparatus of claim 1 wherein the seal forming means is a rigid balloon.

4. The apparatus of claim 1 further comprising a syringe attached to the opposite end of the pipette.

5. A method of artificially inseminating bovines and similar species, comprising:
    providing a conventional bovine insemination pipette;
    providing a rigid tube having a diameter greater than the diameter of the pipette, and an insemination tip formed at the distal end of the tube, the insemination tip having a diameter less than the diameter of the pipette, the insemination tip having an open ejection port at its distal end and at least one lateral ejection port formed on a lateral side thereof, the tube having seal forming means attached thereto behind the insemination tip;
    inserting the distal end of the pipette into the tube so that the tube fits over and attaches to the pipette with the insemination tip abutting the distal end of the pipette;
    guiding the pipette with attached tube and tip into the animal's vagina until the insemination tip is adjacent to the neck of the uterus;
    forming a seal between the tube and vaginal wall behind the insemination tip with the tip between the seal and the neck of the uterus;
    ejecting semen from the pipette through the insemination tip in the uterus of the animal.

6. The method of claim 5 wherein the seal forming means is an inflatable balloon, and the step of forming a seal is performed by inflating the balloon.

7. The method of claim 5 further comprising inserting a speculum into the animal's vagina to locate the neck of the uterus prior to guiding the pipette into the vagina.

* * * * *